(12) United States Patent
McFarland et al.

(10) Patent No.: US 8,340,377 B2
(45) Date of Patent: Dec. 25, 2012

(54) METHOD FOR ENERGY CALCULATION AND PILEUP DETERMINATION FOR CONTINUOUSLY SAMPLED NUCLEAR PULSE PROCESSING

(75) Inventors: Aaron McFarland, Niceville, FL (US); Stefan B. Siegel, Knoxville, TN (US); Danny F. Newport, Clinton, TN (US); Robert A. Mintzer, Knoxville, TN (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 521 days.

(21) Appl. No.: 12/210,464

(22) Filed: Sep. 15, 2008

(65) Prior Publication Data

US 2009/0074281 A1    Mar. 19, 2009

Related U.S. Application Data

(60) Provisional application No. 60/973,083, filed on Sep. 17, 2007.

(51) Int. Cl.
 *G06K 9/00* (2006.01)
(52) U.S. Cl. ................................. 382/128; 250/363.03
(58) Field of Classification Search .................. None
See application file for complete search history.

(56) References Cited

U.S. PATENT DOCUMENTS

| | | | | |
|---|---|---|---|---|
| 4,593,198 A * | 6/1986 | Pang et al. | ..................... | 250/366 |
| 4,612,443 A * | 9/1986 | Alcidi | ........................... | 250/362 |
| 4,835,703 A * | 5/1989 | Arnold et al. | .................. | 702/193 |
| 5,067,090 A * | 11/1991 | Seeman | ............................ | 702/8 |
| 5,225,682 A * | 7/1993 | Britton et al. | ................. | 250/395 |
| 6,160,259 A * | 12/2000 | Petrillo et al. | ............ | 250/363.07 |
| 6,215,122 B1 * | 4/2001 | Clifford et al. | ................ | 250/369 |
| 6,252,232 B1 * | 6/2001 | McDaniel et al. | ............... | 250/369 |
| 6,291,825 B1 * | 9/2001 | Scharf et al. | ................ | 250/369 |
| 6,297,506 B1 * | 10/2001 | Young et al. | ................... | 250/369 |
| 6,310,349 B1 * | 10/2001 | Wong et al. | ............. | 250/363.09 |
| 6,525,322 B2 * | 2/2003 | Wong et al. | ............. | 250/363.09 |
| 6,603,125 B1 * | 8/2003 | Cooke et al. | .................. | 250/369 |
| 6,609,075 B1 * | 8/2003 | Warburton et al. | ............. | 702/87 |
| 6,781,134 B1 * | 8/2004 | Murray et al. | ........... | 250/370.13 |

(Continued)

OTHER PUBLICATIONS

Ksienski, D., et. al., "Numerical methods of noise reduction for frequency domain SEM," Oct. 1984.*

*Primary Examiner* — Vu Le
*Assistant Examiner* — Xuemei Chen
(74) *Attorney, Agent, or Firm* — Peter Kendall

(57) ABSTRACT

A method for processing events in a medical imaging device may comprise the steps of receiving analog signals from at least one PMT into an Applied Specific Integrated Circuit (ASIC) comprising a Constant Fraction Discriminator (CFD) and transmitting analog outputs from the ASIC. Further, sampling the analog outputs continuously using an Analog to Digital Converter (ADC) and transmitting digital outputs; and collecting a number of samples of the digital output during a sampling period using a Field Programmable Gate Array (FPGA) when triggered by the CFD. The method may additionally determine the energy of the analog signals from the at lease one PMT by subtracting the peak value of each signal from the baseline value of each signal, wherein the peak value is determined as an average of at least one sample taken only around the peak during the sampling period, and the baseline value is determined as an average of at least one sample taken only around the beginning or end of the sampling period.

21 Claims, 8 Drawing Sheets

U.S. PATENT DOCUMENTS

| | | | |
|---|---|---|---|
| 6,903,344 B2 * | 6/2005 | Breeding et al. | 250/363.03 |
| 6,936,822 B2 * | 8/2005 | Wong et al. | 250/363.09 |
| 7,208,739 B1 * | 4/2007 | Yanoff et al. | 250/363.09 |
| 7,439,515 B2 * | 10/2008 | Bak | 250/369 |
| 7,573,026 B2 * | 8/2009 | Kurkoski et al. | 250/262 |
| 7,763,859 B2 * | 7/2010 | Mott | 250/369 |
| 7,807,973 B2 * | 10/2010 | Mott | 250/362 |
| 7,855,370 B2 * | 12/2010 | Mott | 250/370.06 |
| 2007/0290126 A1 * | 12/2007 | Kurkoski et al. | 250/262 |
| 2008/0319714 A1 * | 12/2008 | Camus et al. | 702/189 |
| 2009/0032715 A1 * | 2/2009 | Mott | 250/363.01 |
| 2009/0037126 A1 * | 2/2009 | Mott | 702/79 |
| 2009/0039273 A1 * | 2/2009 | Tkaczyk et al. | 250/370.06 |
| 2010/0027747 A1 * | 2/2010 | Mott | 378/82 |
| 2010/0193700 A1 * | 8/2010 | Herrmann et al. | 250/395 |

* cited by examiner

METHOD FOR ENERGY CALCULATION AND PILEUP DETERMINATION FOR CONTINUOUSLY SAMPLED NUCLEAR PULSE PROCESSING

PRIORITY CLAIM

This application claims the benefit under 35 USC 119(e) of U.S. Provisional Application No. 60/973,083 filed on Sep. 17, 2007, the entire contents of which is hereby incorporated by reference in its entirety.

TECHNICAL FIELD

The technical field of the present invention relates to an imaging system. More particularly, the present invention relates to a system and method for a multimodal Positron Emission Tomography (PET), Single Photon Emission Computed Tomography (SPECT), and/or Computed Tomography (CT) imaging system.

BACKGROUND

A multimodal imaging system may comprise PET, SPECT, and CT combined in the same imaging system. Image data acquired from a subject, for example a patient or an animal, may in such as multimodal system derive from all three techniques or a combination thereof.

In CT, an external x-ray source is caused to be passed around a subject, for example an animal or a patient. Detectors around the subject then respond to x-ray transmission through the subject to produce an image of an area of study. Unlike PET, which is an emission tomography technique because it relies on detecting radiation emitted from the subject, CT is a transmission tomography technique which utilizes a radiation source external to the subject.

In SPECT, gamma rays are detected by at least one gamma camera rotating around the subject. Projections are acquired at defined points during the rotation and this information may be presented as cross-sectional slices through the subject, but can be freely reformatted or manipulated as required. The acquired multiple 2-D images, also called projections, may be processed by a computer applying a tomographic reconstruction algorithm to the multiple projections, yielding a 3-D dataset. This dataset may then be manipulated to show thin slices along any chosen axis of the body. SPECT acquisition is very similar to planar gamma camera imaging and the same radiopharmaceuticals may therefore be used. This also allows for possibilities to combine SPECT with other medical imaging processes.

PET is a branch of nuclear medicine in which a positron-emitting radiopharmaceutical is introduced into the body of the subject. Positrons emitted interact with free electrons in the area of interest, resulting in annihilation of the positron. This annihilation yields the simultaneous emission of a pair of photons approximately 180 degrees apart. The radiation resulting from this annihilation is detected by a PET scanner. More specifically, each of a plurality of positrons reacts with an electron in what is known as a positron annihilation event, thereby generating a coincident pair of 511 keV gamma rays which travel in opposite directions along a line of response (LOR). After acquiring these annihilation "event pairs" for a period of time, the isotope distribution in a cross section of the subject can be reconstructed.

A medical imaging device, such as a PET tomograph, is used to detect the positron annihilation events and generate an image of at least portions of the subject from a plurality of detected events. The PET tomograph may comprise a plurality of radiation-sensitive PET detectors arrayed about an examination region through which the subject is conveyed. The PET detectors typically comprise crystals and photomultiplier tubes (PMTs) or Avalanche Photo Diodes (APDs). The detector crystals, referred to as scintillators, convert the energy of a gamma ray into a flash of light that is sensed by the detector, PMT or APD. In coincidence mode a gamma ray pair detected within a coincidence time by a pair of PET detectors is recorded by the PET scanner as an annihilation event. Due to the approximate 180 degree angle of departure from the annihilation site, the location of the two detectors registering the event define the LOR passing through the location of the annihilation. Detection of the LORs is performed by a coincidence detection scheme. A valid event line is registered if both photons of an annihilation are detected within a coincidence window of time. Coincidence detection methods ensure that an event line is histogrammed only if both photons originate from the same positron annihilation. The observed events are typically sorted and organized with respect to each of a plurality of projection rays. By histogramming these LOR, a "sinogram" is produced that may be used by, for example, a process to produce a three dimensional image of the activity. All events occurring along each projection ray may be organized into one bin of a three-dimensional sinogram array. The array may be stored in a computer-readable memory media. The sinogram data is then processed to reconstruct an image of the scanned volume.

Detection of a gamma in one of the crystals may start the events processing chain in several blocks at the same time depending on the sharing design used. A block may contain four PMTs or APDs. The PMTs or APDs convert the light signal from the scintillator into an electrical signal and the connected read-out electronics processes the event by using, for example, printed circuit boards. Accepted events are then transferred to a coincidence controller for further processing. The printed circuit board may have as a main purpose to condition, digitise and process incoming analog pulses from PMT or APD based PET or SPECT detectors.

These printed circuit boards may be analog. Consequently, the reprogramming and adaptation of a medical imaging device, especially the printed circuit boards processing the analog pulses from PMT or APD based PET or SPECT detectors, is cumbersome, if not impossible. It would be desirable to have a medical imaging device that could easily implement and/or test new algorithms or methods for processing the pulses without having to change the hardware.

Another problem is that the high count rate of the gamma causes a problem called pulse pileup, in which two events arrive at the detector so close in time that they produce signals that cannot be separated thoroughly by the electronics. The likelihood of pileup of events increases in a medical imaging device with large block detectors. Developments within the industry lean towards PETs and SPECTs having large block detectors. Electronics able to cope with the increase in events rate is sought after.

A further problem underlying event processing is to obtain a good energy and/or positioning performance from detectors while maintaining high stability across count rates. Additionally, it is desirable to avoid the cumbersome arrangements from a technical and/or economical point of view. Further, low energy consumption and production costs of a medical imaging device are desirable.

SUMMARY

In one embodiment, an event processing module for a medical imaging device may comprise an Applied Specific Integrated Circuit (ASIC) configured for receiving analog signals from at least one PMT and transmitting analog outputs, the ASIC comprising a Constant Fraction Discriminator (CFD); an Analog to Digital Converter (ADC) configured for continuously sampling the analog outputs and transmitting digital outputs; and a Field Programmable Gate Array (FPGA) configured to collect a number of samples of the digital output during a sampling period when triggered by the CFD. Further, the ASIC, ADC, and FPGA may be configured to determine the energy of the analog signals from the at lease one PMT by subtracting the peak value of each signal from the baseline value of each signal, the peak value being determined as an average of at least one sample taken only around the peak during the sampling period, and the baseline value is determined as an average of at least one sample taken only around the beginning or end of the sampling period.

In a further embodiment, the ASIC, ADC, and FPGA may be configured to detect pileup if the current baseline value exceeds a moving baseline value average over a number of previous pulses by more than a predetermined threshold value.

In embodiments, the number of samples may be 16 and the sampling rate may be 100 MHz; the number of previous pulses may be 8. Further, the number of samples may be 32 and the sampling rate may be 200 MHz. The number of previous pulses may be half the number of samples. The number of samples may be any number from 1 to 256; the sampling rate may be any number from 50 to 1000 MHz; and the number of previous pulses may be any number from 2 to 100.

In one embodiment, the ASIC may further comprise a Time to Digital Conversion (TDC) function and pulse shaping and amplification of the received analog signals.

In a further embodiment, the medical imaging device is a multimodal medical imaging device comprising PET, SPECT, and CT combined in the same imaging device.

In embodiments, the analog outputs of the ASIC may be continuously sampled using a 10-bit, 100 MHz ADC. Additionally, the ADC may be an AD9218 ADC from Analog Devices and the FPGA an Xilinx Virtex II Pro FPGA.

In one embodiment, a method for processing events in a medical imaging device, may comprise the steps of receiving analog signals from at least one PMT into an Applied Specific Integrated Circuit (ASIC) comprising a Constant Fraction Discriminator (CFD) and transmitting analog outputs from the ASIC; sampling the analog outputs continuously using an Analog to Digital Converter (ADC) and transmitting digital outputs; and collecting a number of samples of the digital output during a sampling period using a Field Programmable Gate Array (FPGA) when triggered by the CFD. The method may determine the energy of the analog signals from the at lease one PMT by subtracting the peak value of each signal from the baseline value of each signal, wherein the peak value is determined as an average of at least one sample taken only around the peak during the sampling period, and the baseline value is determined as an average of at least one sample taken only around the beginning or end of the sampling period.

In one further embodiment, pileup may be detected if the current baseline value exceeds a moving baseline value average over a number of previous pulses by more than a predetermined threshold value.

In embodiments, the number of samples may be 16 and the sampling rate may be 100 MHz. The number of previous pulses may be 8. The number of samples may be 32 and the sampling rate may be 200 MHz. The number of previous pulses may be half the number of samples.

In embodiments, the number of samples may be any number from 1 to 256 and the sampling rate may be any number from 50 to 1000 MHz. The number of samples may be any number from 1 to 256; the sampling rate may be any number from 50 to 1000 MHz; and the number of previous pulses may be any number from 2 to 100.

In one embodiment, a method for processing events in a medical imaging device, may comprise the steps of receiving analog signals from at least one PMT into an Applied Specific Integrated Circuit (ASIC) comprising a Constant Fraction Discriminator (CFD) and transmitting analog outputs from the ASIC; sampling the analog outputs continuously at 100 MHz using an Analog to Digital Converter (ADC) and transmitting digital outputs; and collecting 16 samples of the digital output during a sampling period of 160 ns using a Field Programmable Gate Array (FPGA) when triggered by the CFD. The method may determine the energy of the analog signals from the at lease one PMT by subtracting the peak value of each signal from the baseline value of each signal, wherein the peak value is determined as an average of the eighth and ninth samples taken around the peak during the sampling period, and the baseline value is determined as an average of the first and second samples taken around the beginning of the sampling period.

At least one embodiment may meet the challenges of event processing and data capture that the high count rates produced by the latest generation of PET systems demand. Using digital pulse processing methods, at least on embodiment may be able to obtain accurate energy and positioning resolution even at count rates well above what would be used in general operation.

At least one embodiment of the printed circuit boards may be able to perform their functions in the digital domain. Consequently, the reprogramming and adaptation of the medical imaging device in question may be done easily. A medical imaging device comprising at least one of the above mentioned embodiments may easily implement and/or test new algorithms or methods for processing the analog pulses from PMT or APD based PET or SPECT detectors without having to change the hardware.

At least one of the embodiments may be able to capture raw event and perform Analog to Digital Conversion (ADC) sampling, allowing for the quick development and comparison of new algorithms in software on actual event samples. Embodiments may be able to cope with the high count rate eliminating the pileup problem. Hereby a medical imaging device with large block detectors may be used.

At least one of the embodiments may allow event processing to obtain a good energy and/or positioning performance from detectors while maintaining high stability across count rates. Additionally, at least one of the embodiments may avoid the cumbersome arrangements from a technical and/or economical point of view.

Other technical advantages of the present disclosure will be readily apparent to one skilled in the art from the following description and claims. Various embodiments of the present application obtain only a subset of the advantages set forth. No one advantage is critical to the embodiments. Any claimed embodiment may be technically combined with any preceding claimed embodiment(s).

BRIEF DESCRIPTION OF THE DRAWINGS

The accompanying drawings, which are incorporated in and constitute a part of the specification, illustrate presently preferred embodiments of the invention, and together with the general description given above and the detailed description of the preferred embodiments given below, serve to explain, by way of example, the principles of the invention.

DETAILED DESCRIPTION

Figure 1:
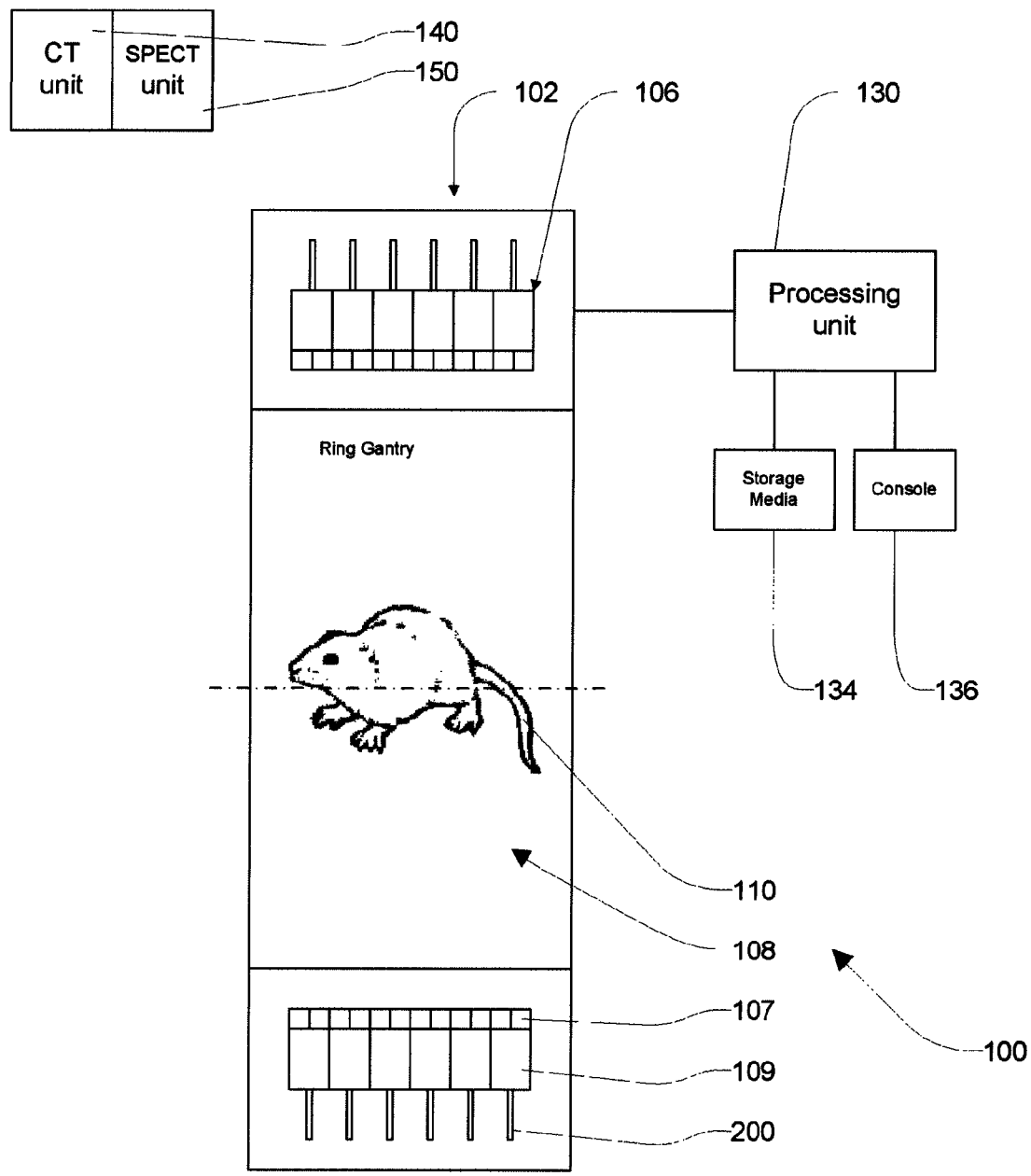
FIG. 1 shows an exemplary embodiment of a medical imaging device.

With reference to the embodiment shown in FIG. 1, a medical imaging device 100, such as a tomograph, for example a PET part of a multimodality system including PET, SPECT, and CT, may include a ring gantry portion 102. A possible combination with CT and SPECT has been indicated by the schematic representation of a CT 140 and the schematic representation of a SPECT 150. The gantry portion 102 includes one or more rings of radiation sensitive detectors 106 which surround an examination region 108, also referred to as the field of view (FOV). The detectors 106 comprise scintillator crystals 107 that convert the energy of each gamma ray characteristic of a positron annihilation event occurring within the PET examination region 108 into a flash of light that is sensed by an APD or PMT 109. A data acquisition system 130 provides annihilation event projection data rebinned into one or more sinogram or projection bins which includes information on the LOR for each event, such as a transverse and longitudinal position of the LOR, its transverse and azimuthal angles, number of events, scan time, etc.

A subject 110 to be imaged may be placed in the FOV 108 of the detectors 106, in coordination with operation of the medical imaging device 100 so that the subject 110 can be scanned. The subject schematically shown in FIG. 1 may be, for example, a small animal, such as for example a rat 110. Such non-invasive imaging may allow a user to monitor, for example, the progression of disease or therapeutic response.

Detection of a gamma in one of the crystals blocks 107 may start the events processing chain in several blocks at the same time depending on the sharing design used. A block may, for example, comprise four PMTs 109 with a crystal array of, for example, 12×12 or 20×20 or more. Any size of crystal array may be used. The PMTs 109 convert the light signal from the scintillator into an electrical signal and the connected read-out electronics processes the event by using, for example, printed circuit boards, such as for example an Event Processing Module (EPM) board 200.

Accepted events are then later transferred to at least one computer or computer processor 130 performing operations on the projection data. The at least one computer or computer processor 130 may use an iterative technique to generate volumetric image data from the projection data. Computer readable instructions which cause the computer 130 to carry out the volumetric image data generation are preferably carried on one or more computer readable media 134 such as computer disks, volatile or non-volatile memory, or the like, and may also be transmitted by way of a suitable communications network such as the internet to storage media 134 accessible to the computer 130. A workstation computer may comprise an operator console 136 and may include a human readable output device such as a monitor or display and input devices such as a keyboard and/or mouse.

The read-out electronics may be based on Field Programmable Gate Arrays (FPGAs) in the EPM board 200. FPGAs may be integrated circuits that consist of a number of identically configurable logic blocks, interconnected by wires and programmable switches. The FPGA may perform digital integration; baseline offset correction and pileup rejection. Programming of the FPGA may be done by the user, who defines the function of the individual blocks and the routing of the connections between the blocks, and thus creates the desired circuit.

This technology provides a high flexibility in the electronics of the medical imaging device, because FPGAs are in-circuit re-configurable, and allow changes of the program equations without any difficulties. Also, they reduce the required amount of electronics, therefore lowering the power consumption and production costs of the medical imaging device.

Figure 2:
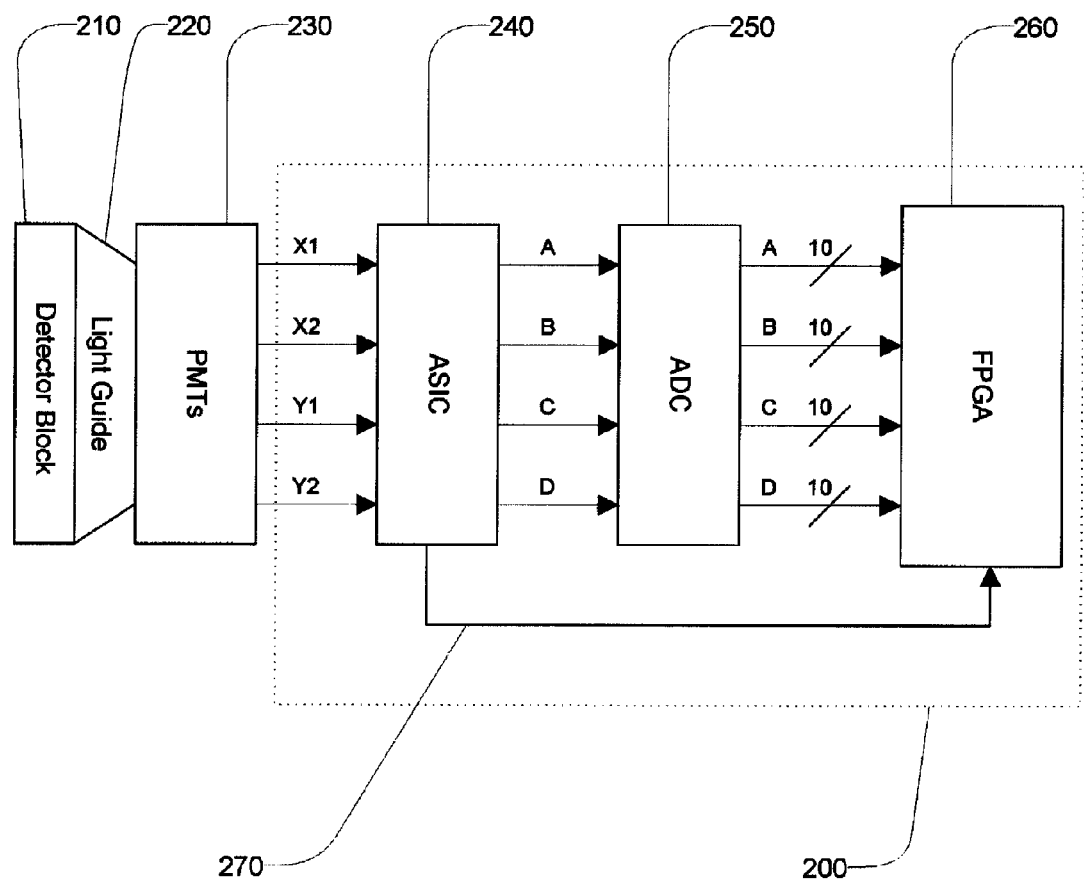
FIG. 2 shows an embodiment of a detector block and its readout electronic as an exemplary PET analog front end block diagram according to an embodiment.

An embodiment of a detector block and its readout electronic is shown in FIG. 2 as an exemplary PET analog front end block diagram. A single PMT may be connected to several detector blocks and each PMT signal may be processed by up to four different electronic channels. Each channel processes the PMT signals, for example PMT signals X1, X2, Y1, Y2, corresponding to a detector block 210. For this purpose use may be made of an analog Application Specific Integrated Circuit (ASIC) 240 with a built-in Constant Fraction Discriminator (CFD), a Time-to-Digital Converter (TDC), an Analog-to-Digital Converter (ADC) 250 and a FPGA 260. The ASIC 250 may be used to generate timing, energy, and position information for every event.

According to an embodiment shown in FIG. 2, the PET scanner detector and readout electronics may comprise a detector block 210, such as for example a Cerium-doped Lutetium Oxyorthosilicate (LSO) block 210. Further the PET scanner and readout electronics may comprise a tapered light guide 220 and position sensitive PMTs (or ADPs) 230. The LSO block 210 may, for example, be a 20×20 mm pixilated LSO block 210. The PMT output may be multiplexed down from 12 to 4 signals X1, X2, Y1, Y2 at the preamplifier and may be sent to an EPM board 200. The EPM board 200 may comprise an ASIC 240 which provides CFD and TDC functions along with pulse shaping and amplification of the analog signals X1, X2, Y1, Y2. The ASIC may be used to generate timing, energy, and position information for every event. The analog outputs A, B, C, and D of the ASIC 240 are then continuously sampled using the ADC 250. Such an ADC may, for example, be a 10-bit, 100 MHz, AD9218 ADC from Analog Devices. The read out may be made by a FPGA 260. Such an FPGA may, for example, be a Xilinx Virtex II Pro FPGA.

According to one embodiment, the acquisition may be done by the FPGA 260 of the EPM board 200. The FPGA 260 may be configured to collect, for example, 16 samples of continuous ADC data when the ASIC CFD triggers; marked as line 270 in FIG. 2. For example, at 100 MHz, this corresponds to 10 ns between each ADC sample for a total sampled time of 160 ns. For the case of fast LSO pulses, even after shaping, this 160 ns window may contain all of the event pulses of interest. The 16 samples may be taken across the A, B, C and D channels simultaneously. Once the 16 samples are acquired for an event, the critical task of calculating the energy of A, B, C, D may be accomplished while accounting for baseline shifts, pileup events and other effects.

The FPGA 260 may be configured to collect any number of samples over a triggered sampling period of time, for example 8, 32 or 64, and this disclosure is not limited to only 16 samples. The ADC may continuously work at a speed of any selected speed, for example 200 MHz, and have a different bit rate, and this disclosure is not limited to only an ADC working at 10-bit and 100 MHz. Any suitable combination of sampling speed may be selected. For example, a higher sampling rate, such as 32 samples at 200 MHz may result in a finer representation of the pulses and a better estimate of the pulse energy.

The energy calculation of an event pulse may be a trade-off between performance and limited FPGA resources. In the analog domain many peak sampling or analog integration techniques have been used in the past to calculate energy. However, in the FPGA energy calculation of an event pulse and peak sampling may be made digitally and therefore with more flexibility.

Figure 3:
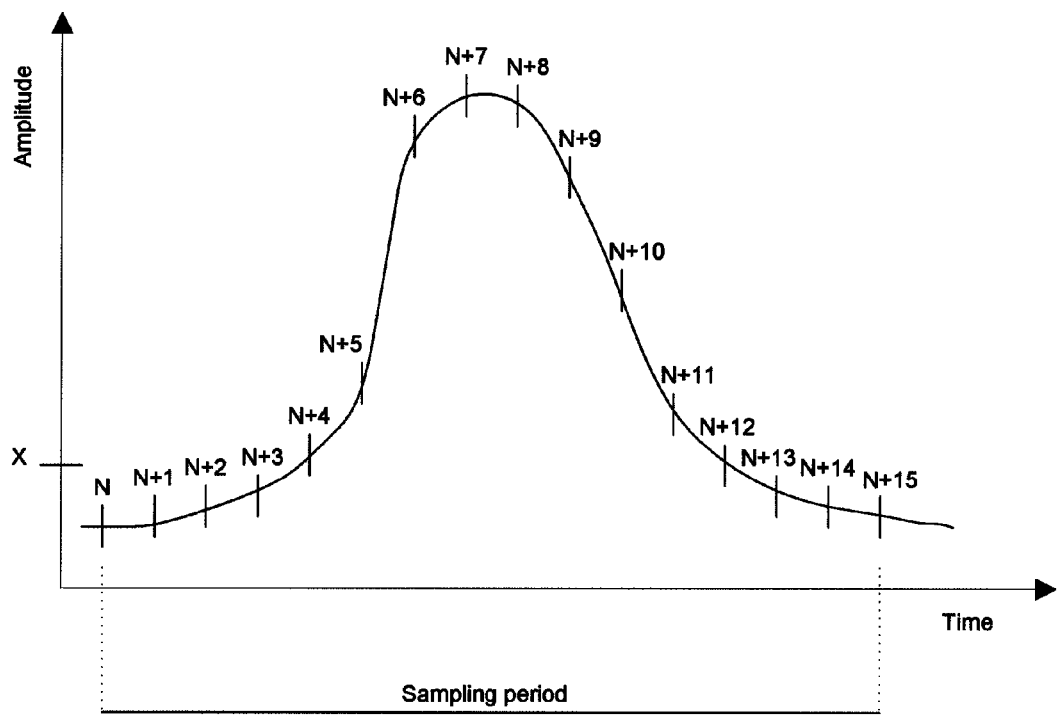
FIG. 3 shows an example of ADC sampling of a PMT shaped pulse as a line chart of time against amplitude according to an embodiment.

An example of ADC sampling of a PMT shaped pulse is shown in FIG. 3 as a line chart of time against amplitude. The exemplary pulse baseline shown in FIG. 3 has been marked with exemplary positions where the sampling may be made. As an example, 16 samples from N to N+15 are marked. As mentioned above, the FPGA 260 may be configured to collect any other number of samples.

In one embodiment, a simple peak minus baseline method was used to calculate energy as shown in FIG. 3, where:

$$\text{Pulse Energy}(A,B,C, \text{ or } D) = N_7 - N_0$$

This embodiment may provide good results for both energy and position with a total block energy resolution of 20% and a position profile peak-to-valley ratio of 2.2 at the block edge. The method may work reasonably well at low count rates.

However, as the count rate increases such a method may become more susceptible to pileup events and baseline changes. While the energy spectra shows little change at increased rates, the event positioning especially for the edge crystals, begins to degrade due to centroid calculation used for computing the event position.

In an embodiment a digital integration method may be used. An average of the samples may be used. With an exemplary number of 16 samples, the pulse energy may be found by subtracting the normalised baseline, as:

$$\text{PulseEnergy} = \left(\frac{\sum_0^{15} N}{16}\right) - N_0$$

This embodiment may show reasonable results with a block energy resolution of again 20% and a position profile peak-to-valley ratio of 2.2. While the digital integration does reduce signal noise caused by the 10 ns uncertainty of the peak (in case of 16 samples at 100 MHz), it is still susceptible to pileup effects especially in the pulse tail. By integrating around the pulse peak, for example using only $N_7+N_8$, and not using the tail, many events that would be skewed due to pileup occurring in the tail may be inherently rejected while still keeping the bulk of the energy information contained in the signal.

An embodiment showing a good balance between the performance, in terms of events considered and rejected, and FPGA resources, in terms of limit on digital logic and processing speed, may be to determine the energy of the analog signal, a pulse from the at lease one PMT, by subtracting its peak value from its baseline value. Pulses from a particular application may maintain a similar pulse shape but change mainly in amplitude. Since pulses for a specific application may mainly differ in the height of the peak value, the embodiment is well adapted for determining the energy of the pulses.

The peak value may be determined with respect to sample(s) taken at or around the peak during the sampling period. Assuming the peak is in the middle of a pulse in a specific application, then, for example, the peak value may be determined as half the sum of at least two samples taken half way through the total numbers of samples, or as a third of the sum of at least three samples taken half way through the total numbers of samples, or as a fourth of the sum of at least four samples taken half way through the total numbers of samples, etc. A peak value taken with only one sample taken half way through the total numbers of samples may also be possible. The peak value may be determined as an average of at least one sample taken only around the peak during the sampling period.

The baseline value may be determined with respect to samples taken at or around the baseline of a pulse. This may be, as shown in FIG. 3, at the beginning or at the end of the pulse. Assuming the peak is in the middle of a pulse in a specific application, then, for example, the baseline value may be determined as half the sum of at least the first (or last) two samples taken, or as a third of the sum of at least the first (or last) three samples taken, or as a fourth of the sum of at least the first (or last) four samples taken, etc. A baseline value taken with only one first (or last) sample may also be possible. The baseline value may be determined as an average of at least one sample taken only around the beginning or end of the sampling period.

An embodiment allows for detection or determination of pileup events and may effectively delete the pileup events from the data string. Pileup may be detected if the current baseline value exceeds a moving baseline value average over a number of previous pulses by more than a predetermined threshold value. If the current baseline, $\text{baseline}_n$, exceeds the moving average of baseline values for a certain number of previous pulses by more than a set threshold, then the current event is determined or identified to contain pileup. On the amplitude axis in FIG. 3, "X" indicates an 8 pulse baseline moving average plus a threshold. While it is possible, but unnecessary, to use a large number of previous pulses, it may be a good balance between performance and FPGA performance to select a moderate number of previous pulses. For example, in a case of 16 samples, the last 8 pulses may be used. This may be expressed as follows:

$$\text{Baseline}_n < \left(\frac{1}{8}\sum_{n=8}^{n}\text{Baseline}\right) + \text{Threshold}$$

Figure 4:
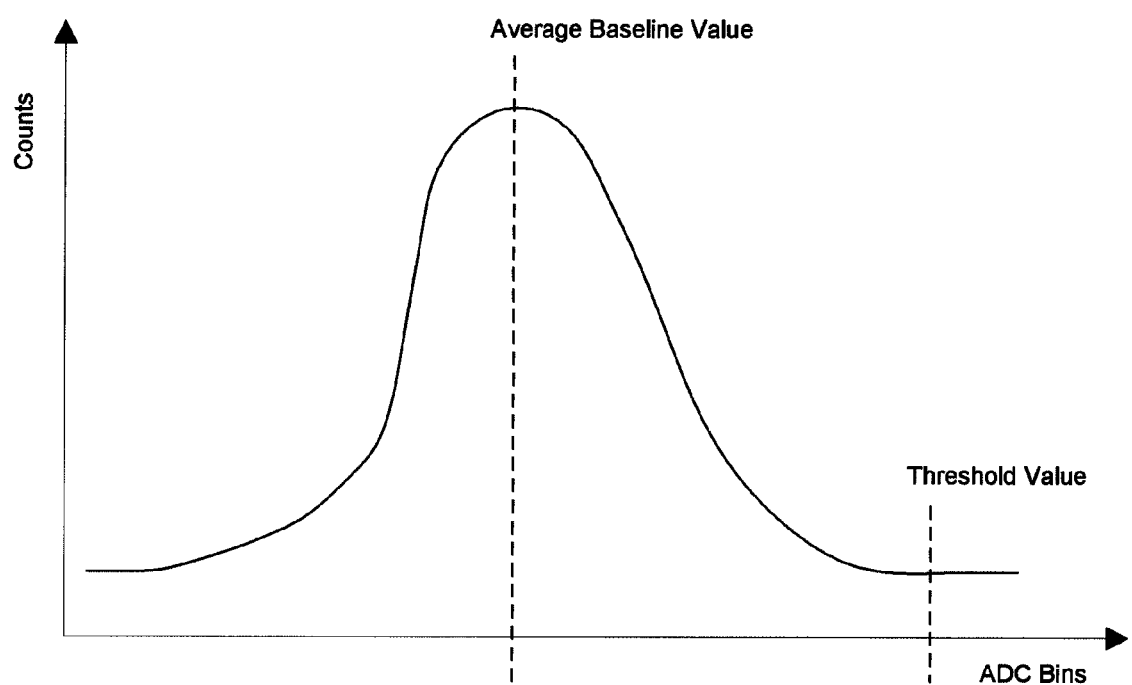
FIG. 4 shows an example of determining a threshold value as a line chart of event counts against ADC bins according to an embodiment

Any number of previous pulses may be used, for example, half the number of samples taken, 5, 10, 15 or any number resulting in an average. The threshold may be determined or selected by histogramming the baseline values of a given application at low pileup conditions; that is at low count rate. This is shown in FIG. 4 as an exemplary embodiment of a line chart of baseline value distribution (in this specific example with 16 samples $(N_0+N_1)/2$) as event counts against ADC bins. The upper threshold limit at which to flag events as pileup is selected as indicated in FIG. 4. The threshold may be selected as the ADC bin value at a point approximately 4 to 5 sigma's from the max of the baseline measurement.

In an exemplary embodiment where sampling is done at 100 MHz by the ADC and 16 samples are collected during a sampling period of 160 ns, the energy of the analog signals from the at lease one PMT may be determined by subtracting the peak value of the signal from the baseline value of the signal, wherein the peak value is determined as an average of the eighth and ninth samples taken around the peak during the sampling period, and the baseline value is determined as an average of the first and second samples taken around the beginning of the sampling period.

Figure 8:
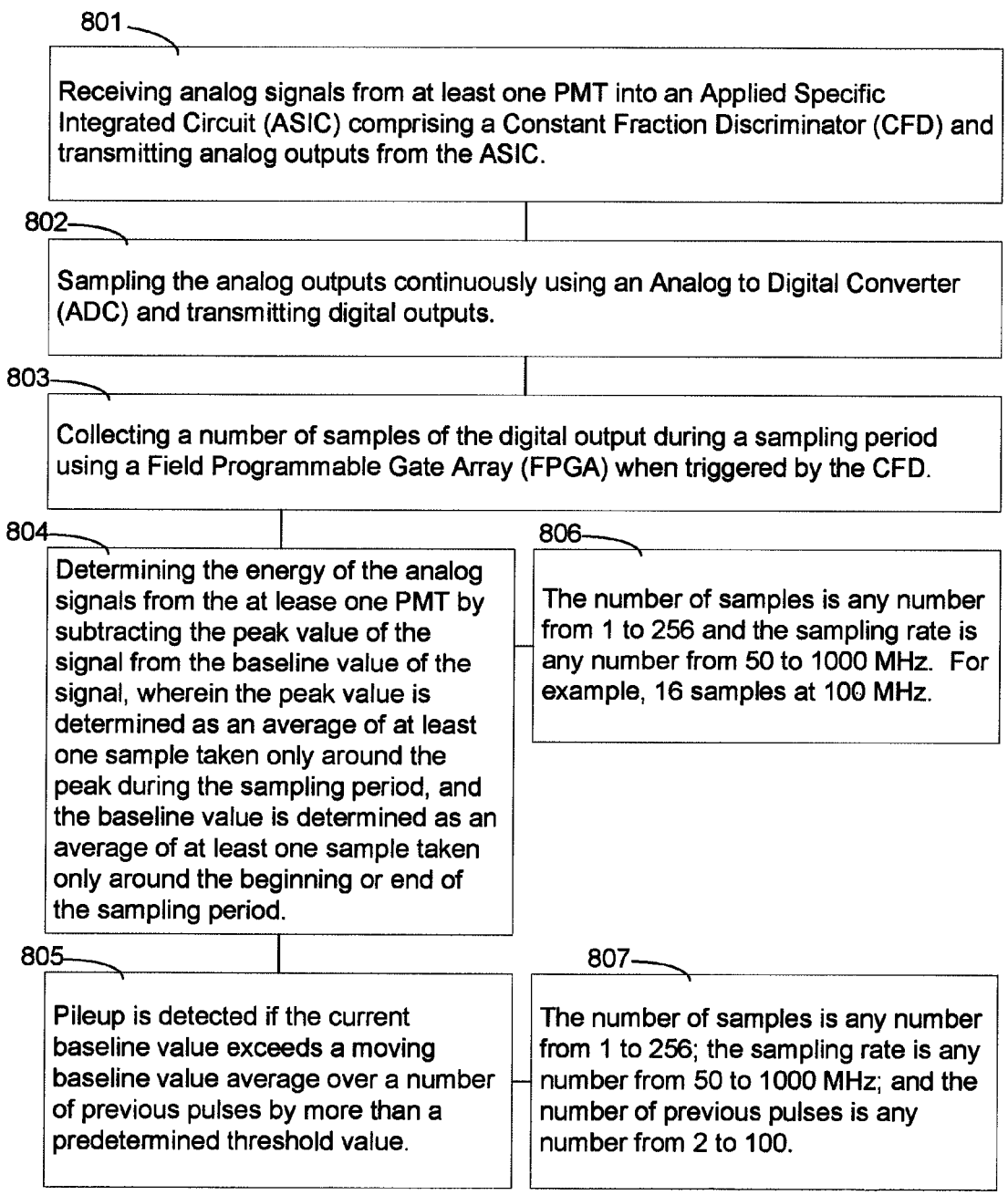
FIG. 8 shows a flow chart of an exemplary method for processing events in a medical imaging device according to an embodiment.

FIG. 8 shows a flow chart of an exemplary method for processing events in a medical imaging device according to an embodiment. In one embodiment a method for processing events in a medical imaging device may comprise the steps of receiving analog signals from at least one PMT into an ASIC comprising a CFD and transmitting analog outputs from the ASIC, as shown in step 801. The analog outputs from the ASIC may be continuously sampled using an ADC and transmitting digital outputs, as shown in step 802. A FPGA may collect a number of samples of the digital output during a sampling period when triggered by the CFD, as shown in step 803.

An embodiment may show a good balance between performance and FPGA resources by determining the energy of the analog signals from the at lease one PMT by subtracting the peak value of the signal from the baseline value of the signal, wherein the peak value is determined as an average of at least one sample taken only around the peak during the sampling period, and the baseline value is determined as an average of at least one sample taken only around the beginning or end of the sampling period. This is illustrated as step 804 in FIG. 8 showing embodiments of the method.

An embodiment may detect pileup if the current baseline value exceeds a moving baseline value average over a number of previous pulses by more than a predetermined threshold value. This is illustrated as step 805 in FIG. 8 showing embodiments of the method.

In embodiments the number of samples may be any number from 1 to 256; the sampling rate may be any number from 50 to 1000 MHz; and the number of previous pulses may be any number from 2 to 100. A specific embodiment may collect 16 samples at a sampling rate of 100 MHz and use the last eight previous pulses.

In the specific example of collecting 16 samples, the energy of the analog signal (event pulse) from the at lease one PMT may be determined by subtracting its peak value from its baseline value, wherein the peak value is determined as half the sum of samples numbers 8 and 9, and the baseline value is determined as half the sum of samples number 1 and 2. Embodiments collecting 16 samples as shown in FIG. 3 may show a good balance between performance and FPGA resources. This would correspond to the following method:

$$Peak = \frac{N_7 + N_8}{2}$$

$$Baseline = \frac{N_0 + N_1}{2}$$

$$PulseEnergy = Peak - Baseline$$

$$\text{Pileup: } Baseline_n < \left(\frac{1}{8}\sum_{n-8}^{n} Baseline\right) + Threshold$$

This embodiment integrates samples at just the peak and leading baseline. Integrating around the peak may provide good signal to noise while not being as affected by pileup in the remainder of the pulse. A moving average of the baseline may be used to reject pileup if the current event's baseline is greater than the moving average value by a set threshold. This method shows improvement in both energy resolution and event positioning over the other two methods due to more accurate A, B, C, D energy calculation and pileup rejection, with a total block energy resolution of 18% and position profile peak-to-valley ratio of 2.2 at the edge, which is an 18% improvement over the first method. At one million CFD triggers per second on a block detector, about 5.9% of events may be rejected as possible pileup using the baseline threshold check.

Figure 5:
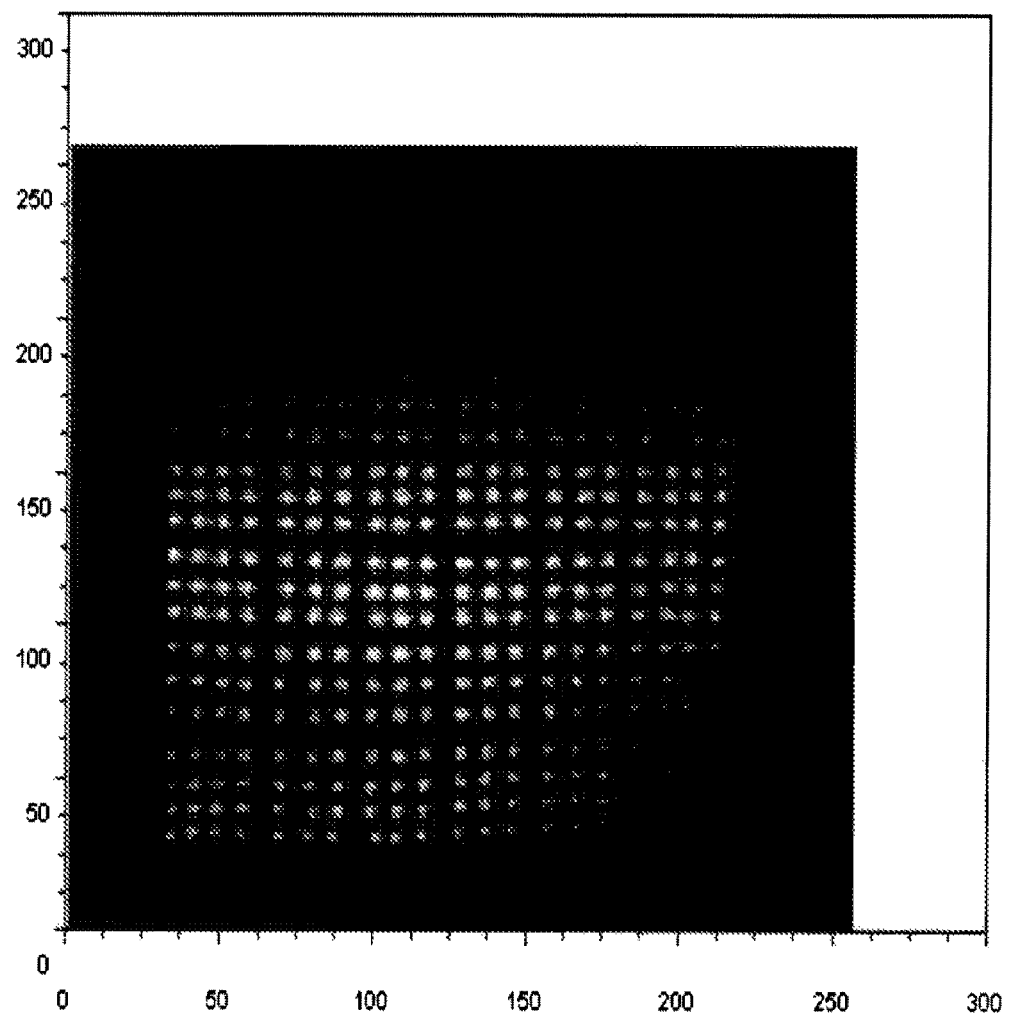
FIG. 5 shows an example of a flood image of an embodiment when all events are accepted.
Figure 6:
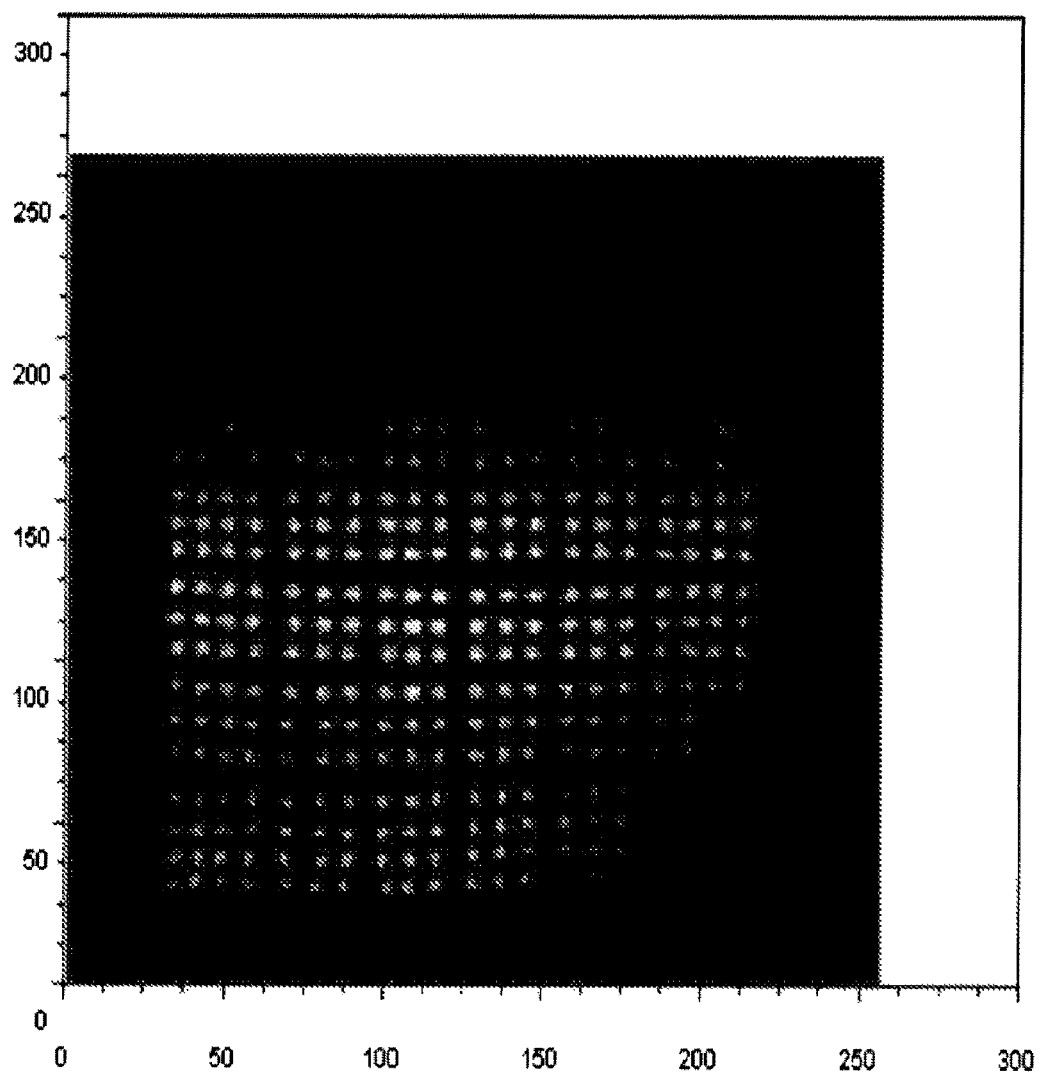
FIG. 6 shows an example of a flood image according to an embodiment.
Figure 7:
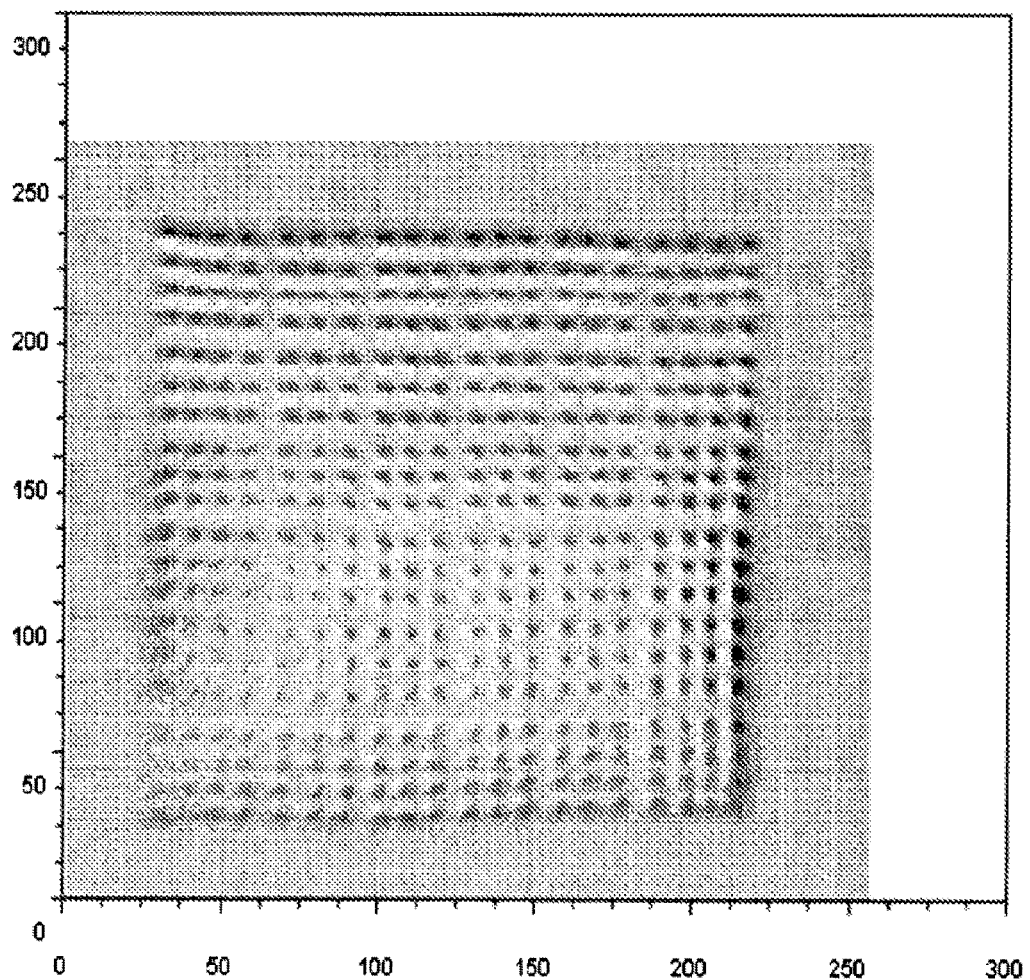
FIG. 7 shows an example of a subtracted flood image from FIGS. 5 and 6 with pixel offset at 1M event/sec.

The improvement may be illustrated by the FIGS. 5 to 7 showing the peak minus baseline flood image along with the results for the above method. FIG. 5 shows a flood image taken when all events are accepted. FIG. 6 shows a flood image for the same detector and set-up as in FIG. 5 but processing the events according to embodiments of the methods or systems described herein. FIG. 7 shows the subtraction of FIGS. 5 and 6 and shows the difference. This difference shown is the improvement in positioning as well as energy measurement for the peaks. At one million CFDs per second, it can clearly be seen that the edge pixel positions have moved inward at this count rate due to pileup versus the new method. This corresponds to a count rate well above the normal, practical injected doses for imaging.

At least one embodiment of the EPM has been designed to meet the challenges of event processing and data capture that the high count rates produced by the latest generation of PET systems demand. Using digital pulse processing methods, the EPM may be able to obtain accurate energy and positioning resolution even at count rates well above what would be used in general operation.

The system and method discussed above are able to capture and process high count rates of pulses. The invention, therefore, is well adapted to carry out the objects and attain the ends and advantages mentioned, as well as others inherent therein. While the invention has been described and is defined by reference to particular preferred embodiments of the invention, such references do not imply a limitation on the invention, and no such limitation is to be inferred. The invention is capable of considerable modification, alteration, and equivalents in form and function, as will occur to those ordinarily skilled in the pertinent arts. The described preferred embodiments of the invention are exemplary only, and are not exhaustive of the scope of the invention. Consequently, the invention is intended to be limited only by the spirit and scope of the appended claims, giving full cognizance to equivalents in all respects.

What is claimed is:

1. An event processing module for a medical imaging device, comprising:
   an Application Specific Integrated Circuit (ASIC) configured for receiving analog signals from at least one photomultiplier tube (PMT) and transmitting analog outputs, the ASIC comprising a Constant Fraction Discriminator (CFD);

an Analog-to-Digital Converter (ADC) configured for continuously sampling the analog outputs and transmitting digital outputs; and a Field Programmable Gate Array (FPGA) configured to collect a number of samples of the digital output during a sampling period when triggered by the CFD;

wherein the FPGA is further configured to determine the energy of the analog signals for the sampling period from the at least one PMT by subtracting a baseline value of the samples from a peak value of the samples, the peak value being determined by selecting a sub-set of one or more of the samples where the sub-set includes fewer than all of the samples having values above the baseline value such that fewer than all of the values above the baseline value are used for determining the energy, the sub-set being selected as the one or more samples taken only around a peak during the sampling period, and by averaging the one or more samples of the sub-set, and the baseline value is determined as an average of at least one sample taken only around a beginning or end of the sampling period, the at least one sample taken only around the beginning or end of the sampling period being taken from the samples during the sampling period triggered by the CFD and not from any samples outside of the sampling period for which the energy is determined; and wherein the FPGA is configured to detect pileup and reject events corresponding to the detected pileup, a pileup being detected if the current baseline value exceeds a moving baseline value average over a number of previous pulses by more than a predetermined threshold value.

2. The event processing module according to claim 1, wherein the number of samples is 16 and the sampling rate is 100 MHz.

3. The event processing module according to claim 1, wherein the number of previous pulses is 8.

4. The event processing module according to claim 1, wherein the number of samples is 32 and the sampling rate is 200 MHz.

5. The event processing module according to claim 1, wherein the number of previous pulses is half the number of samples.

6. The event processing module according to claim 1, wherein the number of samples is any number from 1 to 256; the sampling rate is any number from 50 to 1000 MHz; and the number of previous pulses is any number from 2 to 100.

7. The event processing module according to claim 1, wherein the ASIC further comprises a Time-to-Digital Conversion (TDC) function and is configured for pulse shaping and amplification of the received analog signals.

8. The event processing module according to claim 1, wherein the medical imaging device is a multimodal medical imaging device comprising a positron emission tomography (PET), single photon emission computed tomography (SPECT), and computed tomography (CT) combined in the same imaging device.

9. The event processing module according to claim 1, wherein the analog outputs of the ASIC are continuously sampled using the ADC comprising a 10-bit, 100 MHz ADC.

10. The event processing module according to claim 1, wherein a plurality of PMT signals are multiplexed to n channels and fed to said ASIC and wherein said ASIC generates n output signals; wherein said ADC comprises n input channels and wherein said FPGA has n input channels.

11. The event processing module according to claim 10, wherein n=4.

12. A method for processing events in a medical imaging device, comprising the steps of:

receiving analog signals from at least one photomultiplier tube (PMT) into an Application Specific Integrated Circuit (ASIC) comprising a Constant Fraction Discriminator (CFD) and transmitting analog outputs from the ASIC;

sampling the analog outputs continuously using an Analog to Digital Converter (ADC) and transmitting digital outputs;

collecting a number of samples of the digital output during a sampling period using a Field Programmable Gate Array (FPGA) when triggered by the CFD;

determining the energy of the analog signals for the sampling period from the at least one PMT by subtracting a baseline value of the samples from a peak value of the samples, wherein the peak value is determined by selecting a sub-set of one or more of the samples where the sub-set includes fewer than all of the samples having values above the baseline value such that fewer than all of the values above the baseline value are used for determining the energy, the sub-set being selected as the one or more samples only around the peak during the sampling period, and by averaging the one or more samples of the sub-set, and the baseline value is determined as an average of at least one sample taken only around the beginning or end of the sampling period, the at least one sample taken only around the beginning or end of the sampling period being taken from the samples during the sampling period triggered by the CFD and not from any samples outside of the sampling period for which the energy is determined;

detecting pileup in another sampling period, a pileup being detected if the current baseline value exceeds a moving baseline value average over a number of previous pulses by more than a predetermined threshold value; and reject an event for the other sampling period corresponding to the detected pileup.

13. The method according to claim 12, wherein the number of samples is 16 and the sampling rate is 100 MHz.

14. The method according to claim 12, wherein the number of previous pulses is 8.

15. The method according to claim 12, wherein the number of samples is 32 and the sampling rate is 200 MHz.

16. The method according to claim 12, wherein the number of previous pulses is half the number of samples.

17. The method according to claim 13, wherein the number of samples is any number from 1 to 256 and the sampling rate is any number from 50 to 1000 MHz.

18. The method according to claim 12, wherein the number of samples is any number from 1 to 256; the sampling rate is any number from 50 to 1000 MHz; and the number of previous pulses is any number from 2 to 100.

19. The method according to claim 12, wherein a plurality of PMT signals are multiplexed to n channels and fed to said ASIC and wherein said ASIC generates n output signals; wherein said ADC comprises n input channels and wherein said FPGA has n input channels.

20. The method according to claim 19, wherein n=4.

21. A method for processing events in a medical imaging device, comprising the steps of:

receiving n analog signals multiplexed from m detectors into an Application Specific Integrated Circuit (ASIC) comprising a Constant Fraction Discriminator (CFD) and transmitting n analog outputs from the ASIC, where m and n are integers and m is greater than n;

sampling the n analog outputs continuously at 100 MHz using an Analog to Digital Converter (ADC) and transmitting n digital outputs;

collecting 16 samples of the n digital outputs during a sampling period of 160 ns using a Field Programmable Gate Array (FPGA) when triggered by the CFD, the 16 samples comprising first through sixteenth consecutive samples;

determining an energy of the n analog signals from the at least one photomultiplier tube (PMT) by subtracting a baseline value of the samples from a peak value of the samples, wherein the peak value is determined as an average of the eighth and ninth samples of the first through sixteenth consecutive samples and not including the sixth sample in the average, a value of the sixth sample being greater than the baseline value, the eighth and ninth samples taken around the peak during the sampling period, and the baseline value is determined as an average of the first and second samples taken around the beginning of the sampling period, the first and second samples taken from the samples during the sampling period triggered by the CFD and not from any samples outside of the sampling period for which the energy is determined;

detecting pileup in another sampling period, a pileup being detected if the current baseline value exceeds a moving baseline value average over a number of previous pulses by more than a predetermined threshold value; and reject an event for the other sampling period corresponding to the detected pileup.

* * * * *